(12) United States Patent
Wright et al.

(10) Patent No.: US 6,835,931 B2
(45) Date of Patent: Dec. 28, 2004

(54) CHEMICAL PREFILTERING FOR PHASE DIFFERENTIATION VIA SIMULTANEOUS ENERGY DISPERSIVE SPECTROMETRY AND ELECTRON BACKSCATTER DIFFRACTION

(75) Inventors: Stuart Ian Wright, Orem, UT (US); Matthew McBride Nowell, Draper, UT (US); David Joseph Dingley, South Draper, UT (US)

(73) Assignee: EDAX Inc., Mahwah, NJ (US)

( * ) Notice: Subject to any disclaimer, the term of this patent is extended or adjusted under 35 U.S.C. 154(b) by 0 days.

(21) Appl. No.: 10/439,346

(22) Filed: May 15, 2003

(65) Prior Publication Data

US 2004/0011958 A1 Jan. 22, 2004

Related U.S. Application Data

(60) Provisional application No. 60/380,681, filed on May 15, 2002.

(51) Int. Cl.⁷ .......................................... G01N 23/203
(52) U.S. Cl. ................................... 250/307; 250/310
(58) Field of Search .................................. 250/307, 310

(56) References Cited

U.S. PATENT DOCUMENTS

| | | | |
|---|---|---|---|
| 5,266,802 A | | 11/1993 | Kasai |
| 5,369,275 A | * | 11/1994 | Usui et al. .................. 250/310 |
| 5,557,104 A | | 9/1996 | Field et al. |
| 6,326,619 B1 | * | 12/2001 | Michael et al. ............. 250/310 |

OTHER PUBLICATIONS

Stuart I. Wright, "A Review of Automated Orientation Imaging Microscopy," Journal of Computer–Assisted Microscopy, 1993, pp. 207–221, vol. 5, No. 3, Plenum Publishing Corporation.

Brent L. Adams et al., "Orientation Imaging: The Emergence of a New Microscopy," Metallurgical Transactions A, Apr. 1993, pp. 819–831, vol. 24A.

Stuart I. Wright et al., "Application of a New Automatic Lattice Orientation Measurement Technique to Polycrystalline Aluminum," Materials Science and Engineering, 1993, pp. 229–240, vol. A160.

(List continued on next page.)

*Primary Examiner*—Jack I. Berman
(74) *Attorney, Agent, or Firm*—Webb, Ziesenheim Logsdon Orkin & Hanson, P.C.

(57) ABSTRACT

An analytical method for combining chemical information with crystallographic information to obtain a map of the crystal orientation, the nature of grain boundaries, and distinguishing crystalline phases in a polycrystalline sample, including the steps of providing a sample with a prescribed grid of points thereon, selecting a point, applying a collimated electron beam to the point to obtain an electron backscatter diffraction (EBSD) pattern and the elemental composition of the sample at the point. Recording the information and repeating for each point in the grid and determining the crystalline phases in the sample. An instrument capable of performing the method includes an SEM having means for applying an electron beam to a sample, means for obtaining an EBSD pattern (EBSP), and means for determining the composition of the sample, as well as means for recording EBSD band locations and characteristics and the elemental composition of the sample.

46 Claims, 3 Drawing Sheets

OTHER PUBLICATIONS

D.P. Field et al., "Multi–phase Texture Analysis by Orientation Imaging Microscopy," Proceedings of the 11th International Conference of Textures of Materials (ICOOM–11), 1996, pp. 94–99, International Academic Publishers, Beijing, China.

Stuart I. Wright, "Analysis of Multiphase Materials Using Electron Backscatter Diffraction," Microscopy and Microanalysis, 1997, pp. 561–562, Springer, New York.

N. C. Krieger Lassen et al., "Image Processing Procedures for Analysis of Electron Back Scattering Patterns," Scanning Microscopy, 1992, pp. 115–121, vol. 6, No. 1.

Stuart I. Wright et al., "Automatic Analysis of Electron Backscatter Diffraction Patterns," Metallurgical Transactions A, Mar., 1992, pp. 759–767, vol. 23A.

R. A. Schwarzer, "Advancements of ACOM and Applications to Orientation Stereology," Proceedings of the $12^{th}$ International Conference on Textures of Materials (ICOTOM–12), 1999, pp. 52–61. ed. J. A. Szpunar, NRC Research Press, Ottawa.

K. Kunze et al., "Advances in Automatic EBSP Single Orientation Measurements," Textures and Microstructures, 1993, pp. 41–54, vol. 20.

N.C. Krieger Lassen, "Automated Determination of Crystal Orientations from Electron Backscattering Patterns," Ph.D. Thesis (In particular pp. 58–86), 1994, Danmarks Tekniske Universitet.

* cited by examiner

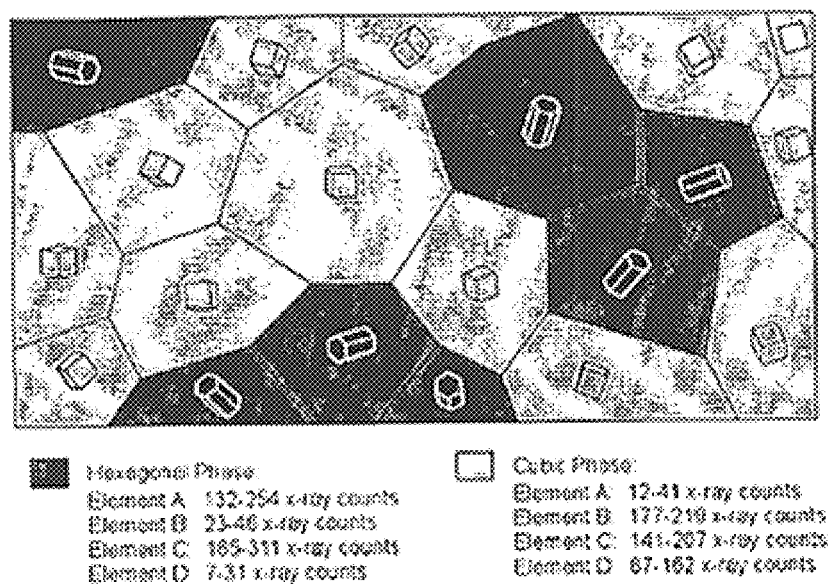
Fig. 1
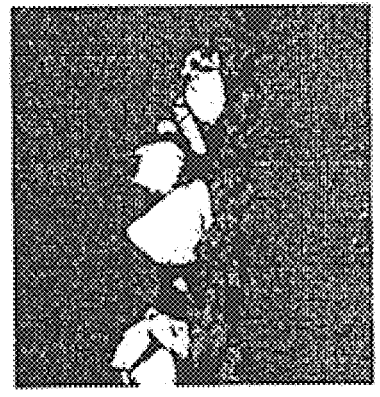
Fig. 2A     Fig. 2B     Fig. 2C

CHEMICAL PREFILTERING FOR PHASE DIFFERENTIATION VIA SIMULTANEOUS ENERGY DISPERSIVE SPECTROMETRY AND ELECTRON BACKSCATTER DIFFRACTION

CROSS-REFERENCE TO RELATED APPLICATION

This application claims the benefit of U.S. Provisional Application Ser. No. 60/380,681, filed May 15, 2002, entitled "Chemical Prefiltering for Phase Differentiation via Simultaneous Energy Dispersive Spectrometry and Electron Backscatter Diffraction," which is hereby incorporated by reference.

BACKGROUND OF THE INVENTION

1. Field of the Invention

The present invention relates to microanalysis techniques for examining material microstructure in a scanning electron microscope or other suitable instrument. In particular, the present invention applies to electron backscatter diffraction in a scanning electron microscope or other suitable instrument to examine the crystallographic aspects of materials.

2. Description of the Prior Art

Electron backscatter diffraction (EBSD) is used by scientists and engineers who need to examine the crystallographic aspects of microstructure. This information can be particularly important in materials used in transportation applications, for example, in aircraft and automobiles. Factors such as crystal orientation and the nature of grain boundaries affect the mechanical and electrical properties of such materials and are, therefore, important design parameters. Unlike X-ray diffraction, EBSD provides scientists and engineers with direct measurements of local orientation that can be correlated with material properties.

Electron backscatter diffraction patterns (EBSP) are obtained in a scanning electron microscope (SEM) by focusing the electron beam on a crystalline sample. The sample is tilted to approximately 70 degrees with respect to the horizontal, and the diffraction pattern is imaged on a phosphor screen. The image is captured using a low-light charge coupled device (CCD) camera or a silicon-intensifier target (SIT) camera. The bands in the pattern represent the reflecting planes in the diffracting crystal volume. Thus, the geometrical arrangements of the bands are a function of the crystallographic orientation and symmetry of the diffraction crystal lattice.

Some success has been documented for differentiating phases by EBSD. However, when the crystallographic structure of two phases are similar it may not be possible to unambiguously distinguish one phase from another using only EBSD.

Energy dispersive spectroscopy (EDS) is a microanalytical technique based on the characteristic X-ray spectrum peaks that are generated when the high energy beam of an electron microscope interacts with a specimen. When a stationary beam of high voltage electrons is focused on a specimen, atoms in the specimen are placed in an excited state. When the excited atoms return to the ground state, they emit an X-ray of characteristic energy and wavelength. This characteristic energy and wavelength is a function of the difference in electron energy levels of the atom. Therefore, each element in a specimen produces an X-ray emission having a characteristic spectral fingerprint that may be used to identify the presence of that element within the specimen.

Some success has been achieved in differentiating phases by EDS. However, when the chemical composition of the two phases are similar it may not be possible to distinguish one phase from another using only EDS.

U.S. Pat. No. 5,266,802 to Kasai discloses an electron microscope having an objective lens and an EDS detector attached thereto.

U.S. Pat. No. 6,326,619 to Michael et al. discloses a method and apparatus for determining the crystalline phase and crystalline characteristics of a sample by using an electron beam generator, such as a scanning electron microscope, to obtain a backscattered electron Kikuchi pattern of a sample, and extracting crystallographic and composition data that is matched to database information to provide a quick and automatic method to identify crystalline phases.

It would, therefore, be desirable to be able to simultaneously collect crystallographic data and chemical data and combine them to obtain reliably differentiated phase data for a sample.

SUMMARY OF THE INVENTION

The present invention is directed to an analytical method for combining chemical information with crystallographic information to obtain a map of the crystal orientation, the nature of grain boundaries and distinguishing crystalline phases in a polycrystalline sample. The method broadly encompasses filtering crystallographic data using the chemical information to provide a map of the crystal orientation and grain boundaries of the sample including the following steps, in any suitable order, of:

providing a list of phases that may be present in a region of interest in a sample to include crystallographic structural parameters for each phase and upper and lower limits for the amount of each element that may be present in each of the listed phases;

identifying the elements present in the region of interest of the sample at a plurality of point locations;

obtaining an electron backscatter diffraction (EBSD) pattern at each of the plurality of point locations in the region of interest;

determining the location of and characteristics of the bands in the EBSD pattern (EBSP);

applying a chemical filter by comparing the amounts of each element at each point against the upper limits and lower limits for a given element with each of the phases in the list of phases to determine a set of possible phases for the point;

assigning a phase to each point by comparing the EBSD band locations and characteristics against the structure parameters for each of the possible phases and determining the best match; and determining the crystallographic orientation of the phase at each of the plurality of point locations in the region of interest.

The present invention is further directed to an instrument capable of performing the above-described method. The instrument generally includes a scanning electron microscope having a means for applying a collimated electron beam to a sample, a means for obtaining an EBSP, and a means for determining the elemental composition of the sample, as well as a means for recording EBSD band locations and characteristics and the elemental composition of the sample.

BRIEF DESCRIPTION OF THE DRAWINGS

FIG. 1 shows a prototype phase map with chemical pre-filtering of the present invention;

FIGS. 2A, 2B, and 2C show EDS maps of titanium, aluminum, and oxygen in a sample respectively;

DETAILED DESCRIPTION OF THE INVENTION

Figure 3:
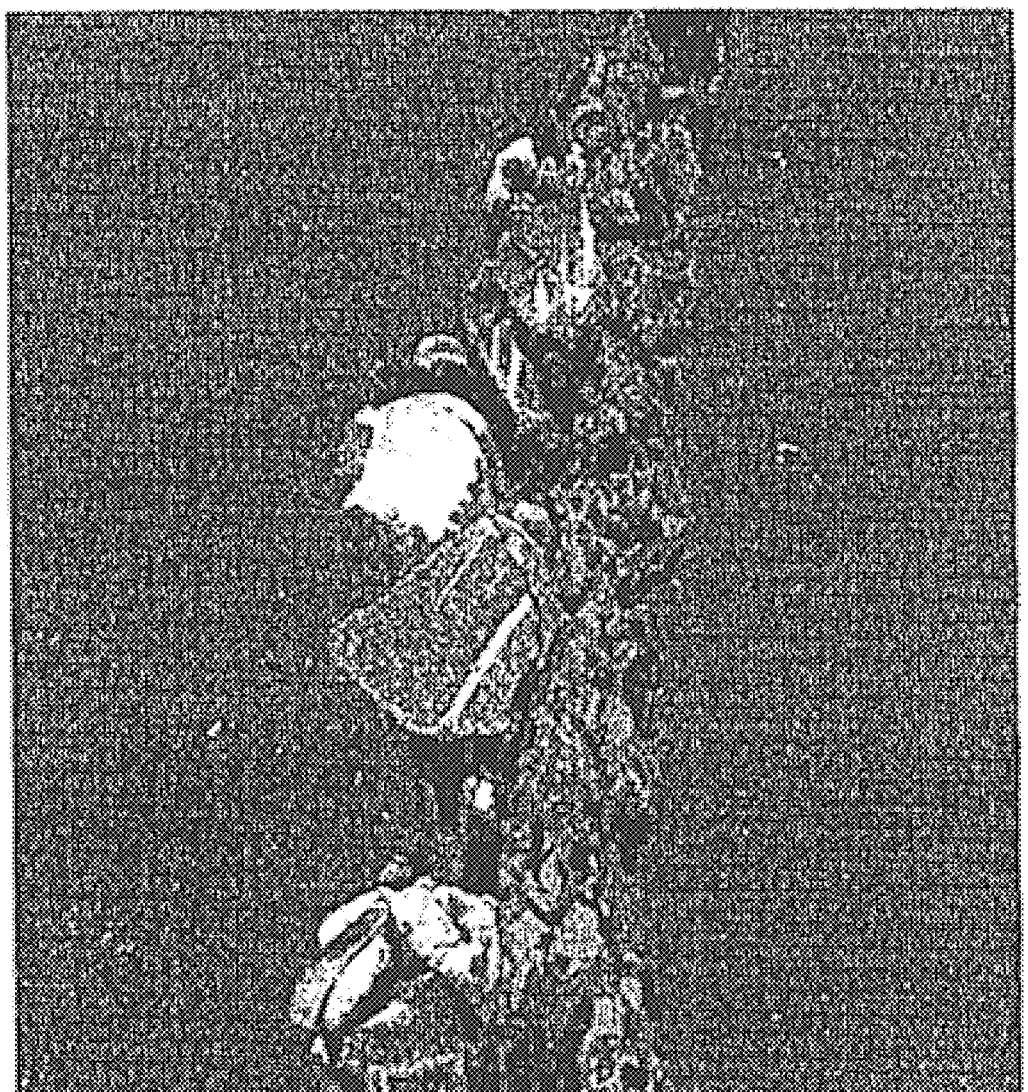
FIG. 3 shows an EBSD phase map of a sample.

As used herein, the term "Phase Differentiation" refers to the process of identifying the phase associated with a point in an automated electron backscatter diffraction (EBSD) scan. In order to perform phase differentiation, the structure parameters associated with each constituent phase must be known a-priori to performing the scan. At each point in the scan, the band information obtained from the corresponding EBSD pattern (EBSP) is compared against the structural information of each of the constituent phases, and the phase whose structure best fits the bands is identified. An integer value denoting the identified phase is recorded in a scan file. (Field et al., "Multi-Phase Texture Analysis by Orientation Imaging Microscopy." Proceedings. Eleventh International Conference on Textures of Materials (ICOTOM-11), Xi'an, China, International Academic: Beijing, 94–99 (1996)).

In the present invention, it is understood that EBSD can be performed using any suitable instrument. Suitable instruments include, but are not limited to, scanning electron microscopes (SEM), Microprobe Analyzers, and Dual Beam Focused Ion Beam (FIB)/SEM instruments. As used herein, any mention of a specific instrument to perform EBSD is meant to include any suitable instrument including those mentioned above.

As used herein, the terms "Phase Identification" and "Phase ID" refer to the process of determining the phase at an individual point in the microstructure. The first step is to determine the chemical composition of the point in question as determined, or at least the chemical elements present at the point using a suitable method, a non-limiting example of such being energy dispersive spectrometry (EDS). This chemical composition is used as a filter against a comprehensive database of phases. The most commonly used database contains nearly 150,000 entries. Phases in the database that have the same chemical composition within prescribed upper and lower limits for each element are identified as candidate phases. An EBSP is then collected from the point and the phase differentiation process is followed using the structural information for each candidate phase.

As noted above, the present method broadly encompasses filtering crystallographic data using the chemical information to provide a map of the crystal orientation and grain boundaries of the sample. The method may include, in any suitable order, the following steps:

providing a list of phases that may be present in a region of interest in a sample to include crystallographic structural parameters for each phase and upper and lower limits for the amount of each element that may be present in each of the listed phases;

identifying the elements present in the region of interest of the sample at a plurality of point locations;

obtaining an EBSP at each of the plurality of point locations in the region of interest;

determining the location of and characteristics of the bands in the EBSP;

applying a chemical filter by comparing the amounts of each element at each point against the upper limits and lower limits for a given element with each of the phases in the list of phases to determine a set of possible phases for the point;

assigning a phase to each point by comparing the EBSD band locations and characteristics against the structure parameters for each of the possible phases and determining the best match; and determining the crystallographic orientation of the phase at each of the plurality of point locations in the region of interest.

In an example embodiment of the present method, EBSD and energy dispersive spectrometry (EDS) can be used as two complementary microanalysis techniques for examining material microstructure in a scanning electron microscope (SEM). In EBSD, patterns are generated by the interaction of an electron beam in the microscope with a sample having a crystalline structure. The bands in the pattern provide information on the crystallographic structure of the sample, as well as the orientation of the crystal lattice relative to a reference frame associated with the sample. The quality of the patterns also provides an indication of perturbations in the crystal lattice within the diffracting volume. Automated routines for indexing the pattern have been developed which enable the orientation of the crystal lattice to be determined.

The method of the present invention may be performed manually, or it may be automated. When the present method as described herein, is automated, the various steps and sequences may be directed by any suitable software program residing on any suitable media. As used herein and in the claims, a suitable software program includes any list of instructions written in a language that may be interpreted by a machine to perform the steps in the present method. As used herein and in the claims, any suitable media includes, but is not limited to, computers, microchips, microprocessors, hard drives, floppy disks, compact disks, and the like.

In the inventive method, a filter is used to distinguish crystalline phases in a polycrystalline sample. Utilizing the filter includes providing a list of phases that may be present in a region of interest in a sample. The information provided for each phase in the list of phases includes crystallographic structural parameters for each phase, and upper and lower limits for the amount of each element that may be present in each of the listed phases. Typically, limits are specified regarding the elemental composition of each phase. Based on the elemental composition at a given point, that point may be assigned one or more possible phases. EBSD band locations and characteristics are compared against the structure parameters for each of the possible phases and a best match between the EBSD data and the structure parameters is determined. Additionally, the EBSD data is used to determine the crystallographic orientation of the phase at various locations in a sample. Thus, the elemental composition, phase, and crystallographic orientation at various locations in a sample can be identified.

In an embodiment of the invention, where multiphase samples are analyzed, it is often necessary to inspect the area to be scanned in the microscope to find the various phases present in the material. Phase ID is then used to classify these constituent phases and obtain the required structural information associated with each phase. Once the constituent phases and their crystallographic structural parameters are identified, this information can be used as input to the phase differentiation process occurring at each point in the automated EBSD scan.

As a non-limiting example, chemical data could be collected for a particular element, aluminum for example. The data collected could be in the form of counts, a scalar value describing the number of X-rays detected of an energy corresponding to aluminum. The number of counts detected at each point in a scan would have a specific range. For a particular point in a scan to be regarded as belonging to a particular phase, it must lie within the pre-determined bounds set by the user for that phase. As a further non-limiting example, in a scan of a sample containing two phases, aluminum oxide ($Al_2O_3$) and pure aluminum (Al), the range of counts for oxygen may range in value from 0 to 300. The bounds for a particular point considered to belong to the aluminum oxide phase may be set at from 30 to 300, and for the pure aluminum phase at less than 30. Thus, the aluminum oxide and pure aluminum phases can be separately identified.

In an embodiment of the present method, an analysis grid made up of a grid of points is prescribed across a surface of the sample. The analysis grid may be a regular array of points where a user specifies the distance between points, the extent of the grid in terms of horizontal and vertical dimensions, and the shape of the grid. The prescribed grid of points may form any suitable shape. Suitable shapes for the analysis grid include, but are not limited to, a square, a rectangle, a hexagon, a circle, an irregular shape, a randomly determined shape, a shape made up of point locations determined from information in a secondary image, and a shape made up of point locations determined from information from a backscattered image. In an embodiment of the present invention, the analysis grid is arranged in a square or hexagonal format. Alternatively, a user may define a custom array where the points in the array need not be equidistant or arranged on regular grid.

In another embodiment of the present invention, the elemental composition of the sample is determined at each point on the analysis grid. The elemental composition of the sample at each point may be determined by any suitable method. Suitable methods for determining the elemental composition include, but are not limited, to energy dispersive spectroscopy (EDS), wavelength dispersive spectroscopy (WDS), cluster analysis, analysis of counts of X-rays within specified energy ranges correlated to specific chemical elements, and energy spectra analysis.

As used herein and in the claims, the term "cluster analysis" and its analogous terms "segmentation analysis" and "taxonomy analysis" refer to a set of techniques for accomplishing the task of partitioning a set of objects into relatively homogeneous subsets based on the clustering of inter-object similarities. "Principal component analysis" is a subset of factor analysis. It is a family of techniques for removing the redundancy from a set of correlated variables and representing the variables with a smaller set of derived variables, or factors.

In EDS, X-rays arising from the interaction of the electron beam and the sample are detected. As different elements produce X-rays at different energies, an energy spectrum is generated. Peaks in the X-ray spectrum can be associated with specific chemical elements.

In the present method, EBSD may be used for two main purposes: phase identification (ID) and orientation mapping. In phase ID, the goal is to identify the specific phase present at a given point of interest in the material microstructure. Phases can be distinguished by chemistry, elemental composition, and crystallographic structure. EDS may be used to identify the chemical elements present in the material. Alternatively, WDS can be used to identify the elements in the material. This information is used as a filter against a comprehensive database of phases to identify candidate phases. EBSD is then used as a second filter to uniquely select from the list of candidate phases the correct phase based on crystallography. This procedure is performed at a single point at a time with user interaction optionally available at each point.

In orientation mapping, the objective is to rapidly determine the crystallographic orientation at each point in a prescribed grid. This can be a highly automated procedure and the scans generally contain arrays of points in the range of tens of thousands to as many as a million data points. Once the user has defined the dimensions of the scan region, no other operator intervention is required in the automated procedure. If the scan area of the sample contains multiple phases, the user also defines the phases present in the scan prior to starting a scan. In polyphase samples, in order to determine the orientation at given point in the scan array, the correct phase is also determined at that point. However, this phase determination process operates on a small set of phases known or assumed to be in scan region and is, hence, called phase differentiation to distinguish from the phase identification procedure. Traditionally, known chemical elemental information is used in the phase differentiation procedure, the differentiation is accomplished solely using the crystallographic information.

In an embodiment of the present invention, the EBSP is obtained by using a scanning electron microscope.

In the present invention, an electron beam, typically a collimated electron beam, is applied to points on the sample to obtain an EBSP and the location and characteristics of the bands in the EBSP are determined at each point. An indexing step may be performed at this point. The EBSP band characteristics may include the intensity of the bands, the geometrical position in the pattern, and the width of the bands.

When an electron beam is focused on the sample surface, the electrons are scattered in a variety of ways. Various detectors are positioned to detect the scattered electrons. Images can be formed by rastering the electron beam across the sample while collecting the intensity of scattered electrons using the various detectors. As non-limiting examples, the detectors in the scanning electron microscopes may be a secondary detector and/or a backscatter detector. A secondary image can be formed by recording the intensities from the secondary electron detector. Similarly, a backscattered image can be formed by recording intensities from the backscattered electron detector.

The indexing step is performed in two parts. First, the bands are detected from the EBSD. This may be done using a procedure based on the Hough transform. The Hough transform is a standard tool in image analysis that allows recognition of global patterns in an image space by recognition of local patterns (ideally a point) in a transformed parameter space. The basic idea of the technique is to find curves that can be parameterized, for example, straight lines, polynomials, circles, etc., in a suitable parameter space. The parameterization reduces the detection of the feature of interest to a peak of characteristic shape in the Hough transform.

In applying the Hough transform in the present invention, the bands are reduced to peaks. The size of the peaks is associated with the width of the bands, and the height of the peaks is associated with the intensity contrast of the bands. The location of the peak in the Hough transform corresponds to the position of the band in the diffraction pattern. Once the bands are located in the pattern, the angles between the bands are compared against theoretical look-up tables built up from known crystal structures. It is also possible to use the width and intensity contrast of the bands to make the indexing procedure more stringent.

In a further embodiment of the present invention, the recording of the location and characteristics of the bands in the EBSP may include recording specific information about the diffraction bands and data derived from a suitable automated band detection algorithm. A non-limiting example of a suitable automated band detection method for analyzing EBSPs is the above-mentioned Hough transform. In the Hough transform, a pattern is transformed according to the equation $\rho = x_i \cos\theta_k + y_i \sin\theta_k$, where $x_i$, $y_i$ coordinates of $i^{th}$ pixel in an EBSP. This function maps a point in the x, y pattern space to a series of points in Hough space ($\rho$, $\theta$ space). For the implementation into a computer, Hough space is discretized into a bounded array, where $\theta$ will range in value from 0 to 180 degrees and the bounds of $\rho$ are dependent on the size of the EBSP. The array is constructed by discretizing the parameters ρ and θ into discrete steps. As a non-limiting example, θ may range from 0 to 180 degrees in 1 degree steps and for a 256×256 pixel EBSP, ρ would range in value from −181 to +181 in steps of 2. An accumulator array is constructed of the form $H(\rho_l, \theta_k)$. For each pixel $(x_i, y_i)$ in the EBSP (or some predefined subset of the EBSP), ρ is calculated for each $\theta_k$. ρ is necessarily rounded to the nearest value discrete value $\rho_l$. The accumulator array is incremented at each value of $(\rho_l, \theta_k)$ by the gray level of the pixel, $I(x_i, y_i)$.

The utility of the Hough transform of the EBSP is that lines of high intensity in the EBSP become peaks in the transform. The problem of detecting the lines (or bands) is then reduced to finding peaks of high intensity in the transform. The bands in the EBSPs are generally characterized by the center of the bands having high intensity and the edges of the bands having low intensity. Thus, to improve the band detection algorithm, not only is the transform searched for peaks of high intensity but the accompanying valleys of low intensity are also checked. The application of the Hough transform to EBSPs is disclosed generally by Kunze et al., "Advances in Automatic EBSP Single Orientation Measurements," *Textures and Microstructures* 20: pp. 41–54 (1993) and Lassen et al., "Image Processing Procedures for Analysis of Electron Back Scattering Patterns," *Scanning Microscopy* 6 pp. 115–121 (1992).

A further non-limiting example of a suitable automated band detection and location method for analyzing EBSPs is the Radon transform, which is used to transform two dimensional images with lines into a domain of possible line parameters, where each line in the image will give a peak positioned at the corresponding line parameters. The Radon transform is described in, for example, Lassen, *Automated Determination of Crystal Orientations from Electron Backscattering Patterns*, Ph.D. Thesis, Danmarks Tekniske Universitet (in particular pp. 58–86) (1994) and Schwarzer, "Advancements of ACOM and applications to orientation stereology," *Proceedings of the Twelfth International Conference on Textures of Materials*, ed. J. A. Szpunar, NRC Research Press: Ottawa, (1999) pp. 52–61.

An additional non-limiting example of a suitable automated band detection and location method for analyzing EBSPs is the Burns algorithm, an edge detection routine. Application of the Burns algorithm to EBSPs is described by Wright et al., "Automatic Analysis of Electron Backscatter Diffraction Patterns," *Metallurgical Transactions* A 23 (1992) pp. 759–767. The first step in the Burns algorithm is to calculate the image gradient of the EBSP. This is done by convoluting the pattern with two edge detection masks (the so-called Sobel filters). The two filters produce two convoluted images. In one image, each pixel is replaced by the magnitude of the local gradient in the horizontal direction. In the second image, each pixel is replaced by the magnitude of the local gradient in the vertical direction. A vector specifying the magnitude and direction of the local intensity gradient can then be determined at each pixel by combining the data from the two convoluted images. A search is then made to look for sets of neighboring gradient vectors in the image with similar direction. These are then assumed to represent edges of the diffraction bands in the EBSP. For each "edge group," a search is made of a parallel edge group. If two parallel edge groups are found, then a diffraction band is detected.

The sample in the present invention may be any crystalline sample having any crystallographic symmetry. As used herein and in the claims, the term "crystallographic symmetry" refers to crystalline materials, such as metals, ceramics, and minerals, which are made up of atoms arranged in a periodic lattice, such as a cube or a hexagon. The crystal lattice may have some degree of rotational symmetry associated with it. This indicates that a specific rotation about a specific axis will result in the crystal lattice being in an orientation that cannot be distinguished from the original orientation. As a non-limiting example, a cubic crystal having a single atom of the same element may be located at each of the 8 corners of the cube, one symmetric rotation would be a rotation of 90 degrees about an axis normal to one of the faces of the cube. Another symmetric rotation would be a rotation of 120 degrees about the body diagonal of the cube. The set of symmetric rotations defines the crystallographic symmetry.

An embodiment of the present invention is directed to a method of filtering data from an SEM map of a sample. In the method, the SEM acquires EDS data from an X-ray detector and EBSPs from an electron backscatter "detector" (the detector in this sense typically includes a phosphor screen on which an EBSD pattern is formed, the pattern is imaged using a low light camera such as a charge coupled device (CCD) camera or a silicon intensified target (SIT) camera), and links the EDS data and the EBSD data such that the EDS chemical information from the sample is used to filter a list of provided candidate phases prior to performing phase differentiation analysis of the EBSPs.

In a further embodiment of the present invention, the location and characteristics of the bands in the EBSP are compressed before being recorded. Further to this embodiment, the location and characteristics of the bands in the EBSP are stored on appropriate storage media in a suitable computer for storing such data. In this embodiment, a pattern is stored in the computer's memory as scalar intensity at each point in the analysis grid, each point being indicated as a row and column in a table. Typically, the scalar intensity ranges in value from 0 to 256, although higher resolution patterns can also be recorded at wider ranging values. Various compression routines are available for recording the patterns on computer storage media, such as hard drives or CD-ROMs. Any suitable compression format known in the art may be used, a non-limiting example of an acceptable compression format is the Joint Photographic Experts Group (JPEG) format.

As stated above, the steps in the present method may be performed in any appropriate order. As a non-limiting example and a particular embodiment of the present invention, the method of distinguishing crystalline phases in a polycrystalline includes:

(a) providing a sample;

(b) selecting a region of interest on the sample;

(c) providing a list of phases that are either known or assumed to be present in the region of interest to include crystallographic structural parameters for each phase and upper and lower limits for the amount of each element that may be present in each of the listed phases;

(d) identifying the elements present in the region of interest;

(e) prescribing a grid of points across a surface of the sample;

(f) selecting a point on the grid;

(g) applying an electron beam to the point;

(h) obtaining an EBSP;

(i) determining the location of and characteristics of the bands in the EBSP;

(j) measuring the amounts of each element in (d) at the point;

(k) recording the location of the point on the sample, the EBSD band locations and characteristics in (i) and the amounts of each element in (j) as a line in a scan grid file;

(l) repeating (f) through (k) for each point on the prescribed grid to generate a complete scan grid file;

(m) selecting a line from the scan grid file;

(n) applying a chemical filter by comparing the amounts of each element against the upper limits and lower limits for a given element with each of the phases in the list of phases in (c) to determine a set of possible phases for the point;

(o) assigning a phase to the point by comparing the EBSD band locations and characteristics against the structure parameters for each of the possible phases and determining the best match;

(p) determining the crystallographic orientation of the phase at the point;

(q) recording the point location, elemental composition, assigned phase, and crystallographic orientation in a phase grid file;

(r) repeating (m) through (q) for each line in the scan grid file.

As another non-limiting example and a further particular embodiment of the present invention, the method of distinguishing crystalline phases in a polycrystalline includes:

(a) providing a sample;

(b) prescribing a grid of points across a surface of the sample;

(c) selecting a point on the grid;

(d) applying a collimated electron beam to the point;

(e) determining the elemental composition of the sample at the point;

(f) recording the location of the point on the sample, the EBSD band locations, and the elemental composition;

(g) repeating (c) through (f) for each point on the prescribed grid;

(h) specifying limits on the elemental composition of each phase;

(i) specifying the crystallographic parameters of each phase;

(j) assigning each point to a phase based on the elemental composition of the sample for each point;

(k) selecting a point on the grid in (b);

(l) applying a collimated electron beam to the point;

(m) obtaining an EBSP;

(n) determining the location of and characteristics of the bands in the EBSP;

(o) recording the location of the point on the sample and the EBSD band locations and characteristics;

(p) repeating (k) through (o) for each point on the prescribed grid; and (q) combining the EBSD band characteristics and the phase information in (j) to determine the crystallographic orientation for each point.

Each of the individual steps indicated above may be accomplished as previously indicated.

In the method of the present invention, for each point in the analysis grid, the location of the point on the sample, the EBSD band locations and characteristics, and the elemental composition are recorded. From this information, the crystalline phases in the sample are determined.

In an embodiment of the present invention, the crystalline phases in the sample may be determined by specifying limits on the elemental composition of each phase, specifying the crystallographic parameters of each phase, assigning each point to a phase based on the elemental composition of the sample for each point, and determining the crystallographic orientation for each point from the characteristics of the bands in the EBSP for each point.

Maps may be used to visualize the crystallographic and chemical data acquired using suitable techniques, EBSD and EDS being non-limiting examples thereof. In EBSD, the technique used may be orientation imaging microscopy (OIM). In OIM, the beam is stepped across the sample and at each point in the scan an EBSP is generated. The orientation of crystal lattice can be determined by automated analysis of the patterns. In materials made up of multiple crystal structures or phases, not only is the orientation determined during the scanning procedure but also the phase is determined. This requires that the phases in the material be known a-priori. Each pattern is indexed, assuming each candidate phase and the phase that seems to fit the pattern best are identified. This procedure may be referred to as phase differentiation. In order to reduce the amount of time physically spent at the microscope, it is possible to record the patterns (or some critical parameters associated with the patterns arising during the indexing procedure, such as the Hough peak data) and then perform the analysis offline. Once the orientation and phase at each point in a scan are determined, maps can be constructed from the data.

EDS maps can be formed in a similar manner. As the beam is stepped across the sample, the X-ray counts detected for a given energy range are recorded. This can be done for several energy ranges. Each energy range is associated with a particular element. Thus, a map can be generated by assigning a color to each point in the scan based on the number of counts for a particular element. This enables the spatial distribution of a given element to be visualized.

In SEMs meeting specific geometric requirements, it is possible to simultaneously collect the chemical information via EDS and the crystallographic information via EBSD. This allows maps to be created or generated and correlations between the chemistry and crystallography to be explored. The present method is unique because chemical and crystallographic data are coupled together during the indexing procedure.

Typically, the maps that are prepared using the present method indicate the various phases by varying the colors of each phase along a color continuum or a grayscale continuum. This enables the viewer to readily discern the number, nature, and interrelation of the various phases within a sample. Typically, each phase is designated by a different color or shade of gray.

FIG. 1 shows a prototype map of the present invention. The map shows a theoretical sample containing various amounts of elements A, B, C, and D, and having a hexagonal phase (indicated by hexagonal cylinders) and a cubic phase (indicated by cubes). The compositional phases are determined by the number of counts detected for each of the four elements. The map shows the phase boundaries based on the shape and orientation of the crystal structure and the elemental composition of the phase.

The present method, coupling is advantageous because, for some materials, it is difficult to distinguish between phases by simply using an analysis of the EBSPs. As an example, where it is difficult to distinguish between the large particles near the center of the map and the matrix material on either side in the EBSD analysis, the larger particles in the center of the map may not be distinguishable. With the more stringent EBSP analysis of the present invention, it is possible to improve the phase differentiation. The difference between the matrix material and the large particles then becomes obvious in the chemical maps. The present invention is directed to utilizing this chemical information to identify the phase so it can be used to improve the phase differentiation capabilities in the combined EBSD/EDS mapping system.

In an embodiment of the present invention, the following approach can be taken to implement such a "prefiltering" of the EBSD phase differentiation based on chemistry.

First, the elements that are present in the material in the area to be examined are identified. This can be done by obtaining a spectrum while rastering the beam over the area of the sample of interest. This produces an overall spectrum for the area of interest. The peaks in the spectrum can then be identified with specific chemical elements.

Next, a scan is performed on the area of interest. At each point in the scan, the Hough peaks are determined and recorded. Additionally, the X-ray counts for each identified element are recorded. Once the scan is completed, this data may be analyzed offline. For each candidate phase, a range of allowed counts is set for each element. Thus, if one phase contains aluminum and titanium and another phase contains aluminum and oxygen, then the first phase would have a wide allowed range for aluminum and titanium but a narrow range for oxygen; conversely, the second phase would have a wide range for aluminum and oxygen but a narrow range for titanium. This set of ranges then acts as a chemical prefilter to the standard EBSD-based phase differentiation routine.

Subsequently, for each point in the scan, the candidate list of phases is reduced to those satisfying the chemistry filter. The standard crystallography-based phase differentiation routine is performed, and the phase and orientation is recorded in the scan file.

In an embodiment of the present invention, the method includes recording EDS counts at each point in the scan for some prescribed energy ranges corresponding to specific chemical elements, recording the Hough peak data at each point, and after completing the scan, post-processing the data. At each point, the list of candidate phases is filtered based on some prescribed limits on the EDS counts for each element. The phase differentiation is then performed on the reduced candidate list based on the Hough peak data.

The method of the present invention may be performed online, however, this may take more time than the offline approach described above. Because SEM time is usually critical (and expensive), the offline approach is presently preferred. In addition, the offline approach has the advantage that the minimum and maximum counts are known after all of the data is collected, making it much easier to set up the ranges for the filter.

In an embodiment of the present invention, the automated EBSD scanning software sets the stage for the prefiltering concept by saving the Hough peaks at each point in the scan and/or simultaneously collecting the EDS data.

Other approaches to implementing the chemical prefiltering of the present invention may be included. In an embodiment of the invention, instead of saving the EBSP data, the pattern could be indexed for each of the candidate phases, and the orientation for each phase could be recorded. The chemical filter could then be applied and the candidate phase selected based on chemistry. The associated orientation would also be selected in this process.

In a further embodiment of the invention, the spectrum is recorded at each point in the scan. In this approach, instead of using the counts within specific energy ranges, the complete spectrum could be analyzed and checked against a characteristic footprint for the chemical content of each phase. In some microscopes, the electron beam loses intensity during a scan. This would cause the average number of EDS counts to decrease as a scan proceeds. Thus, instead of using absolute counts for differentiating between phases, it would be more productive to use count ratios between the various elements used in the filtering procedure. In addition, chemistry prefiltering could also be based on other parameters, such as the overall pattern quality or the magnitude of the signal from a forward-scatter detector, both of which may vary (on average) with the phase.

In an additional embodiment of the present invention, being able to simultaneously collect EDS and EBSD data may not be necessary. The chemical information required in filtering the database may be derived from the EDS system and then entered manually into the EBSD system to complete the phase differentiation procedure. In this system, a user filters the data based on some parameter, most likely chemical content, and reassigns the filtered data to a specific phase. This type of approach is best suited for cubic materials as the orientation is the same regardless of the phase selected.

In an another embodiment of the present invention, instead of examining absolute counts within an energy range, ratios in counts for energy ranges corresponding to different elements in a region of interest could be used. In a further embodiment, instead of using counts, a spectrum could be analyzed for peak height (or volume) for specific elements. As with the region of interest counts, ratios derived from the peak height or volume data could be used as well. In addition, peak identification and quantification could be performed on the spectrum, and this information could be used to filter the candidate phase list. Another approach would be to obtain X-ray maps from the scan area. A subset of the candidate phase list could be assigned to areas in the maps exhibiting specific composition ranges.

In a further embodiment of the present invention, instead of performing phase differentiation in the standard ranking approach, other approaches could be used. This includes using angles between bands, bandwidths, and/or band intensity measures. Instead of using Hough data, the patterns could be analyzed via other techniques, such as the Burns method, to extract the information on the bands and their geometrical arrangement in the EBSPs. Instead of recording the Hough data at each point in the scan, the pattern itself or the Hough transform could be recorded instead.

In yet a further embodiment of the present invention, instead of performing the chemical assisted phase differentiation in a post-processing mode, the chemical assisted phase differentiation could be performed online. At each point in the scan, the chemical information could be obtained, and the candidate list could be filtered. The EBSD analysis could then be performed and the results recorded. Another mixed online/offline approach would be to record the chemical information (counts or spectra) at each point, attempt to differentiate the phases via the EBSD, and record the results for each phase. At completion of the scan, selecting from the solutions for each phase based on the chemistry is desired.

In an additional embodiment of the invention, the levels for the filters could also be constructed a-priori by performing the chemical analysis on a few selected points prior to performing a full scan.

In a further embodiment of the invention, at each measurement point in the scan, instead of recording counts within specific energy ranges, a full spectrum is recorded. "Cluster," "principal components," "multivariate statistical," or "chemometric" analysis is then applied to the data set as whole. These methods identify potential "spectral" or "chemical components" from an array of spectra collected over a spatial dimension (a "spectral image"). A potential list of crystallographic phases can be assigned to each of the relevant chemical components. The potential phases associated with a scan measurement point are then assigned based on the component to which the pixel belongs or is most closely associated with instead of comparing against levels defined by the user.

The present invention is also directed to an instrument for determining the crystallographic aspects of materials. The instrument will typically include a scanning electron microscope that has a means for applying a collimated electron beam to a sample, a means for obtaining an EBSP, and a means for determining the elemental composition of the sample along with a means for recording EBSD band locations and characteristics and the elemental composition of the sample. As indicated above, the characteristics of the bands in the EBSP may include the intensity of the bands, the geometrical position in the pattern, and the width of the bands. The means for determining the elemental composition of the sample may be selected from energy dispersive spectroscopy, cluster analysis, analysis of counts of X-rays within specified energy ranges correlated to specific chemical elements, and energy spectra. Also, as indicated above, the location and characteristics of the bands in the EBSP may be compressed before being recorded. Further, the instrument may include a means to automate the instrument to carry out the present method as described above.

Figure 4:
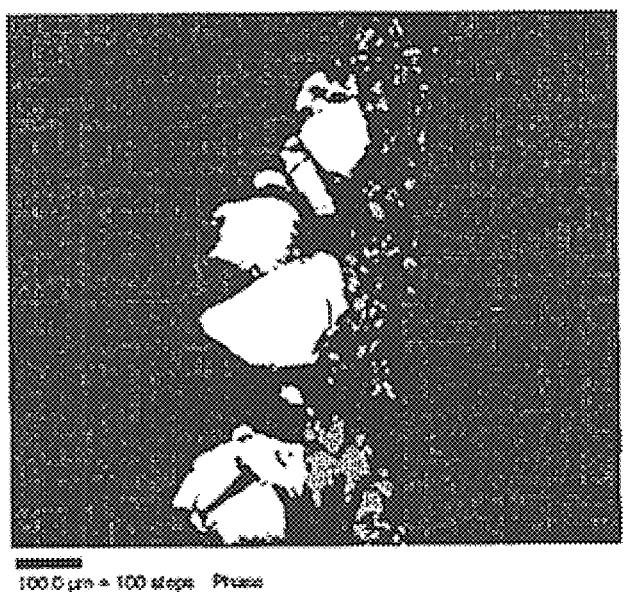
FIG. 4 shows a phase map acquired using the chemical pre-filtering method of the present invention.

The method of the present invention is demonstrated in the following example. An analysis grid was prescribed over a sample. Using a scanning electron microscope, an EDS X-ray spectrum and an EBSP were collected for each point in the analysis grid. After the orientation (EBSD) and phase (EDS) were determined at each point in the analysis grid, maps were constructed. The maps were generated by assigning a color to each point in the scan based on the orientation of the crystal and/or the amount of a given element in the crystal. FIG. 2A shows an EDS map for titanium, FIG. 2B shows an EDS map for aluminum, and FIG. 2C shows an EDS map for oxygen, all in gray scale. FIG. 3 shows a gray scale EBSD map for the sample. The present coupling method is advantageous because, for some materials, it is difficult to distinguish between phases by simply using an analysis of the EBSPs. An example is shown in FIG. 3, where it is difficult to distinguish between the large particles near the center of the map and the matrix material on either side in the EBSD analysis. This sample was reanalyzed using the present method. As shown in FIG. 4, the various phases are clearly visible on the chemical pre-filtered map.

It will be appreciated by those skilled in the art that changes could be made to the embodiments described above without departing from the broad inventive concept thereof. It is understood, therefore, that this invention is not limited to the particular embodiments disclosed, but is intended to cover modifications which are within the spirit and scope of the invention as described herein and in the accompanying claims.

We claim:

1. A method of distinguishing crystalline phases in a polycrystalline sample comprising:

providing a list of phases that may be present in a region of interest in a sample to include crystallographic structural parameters for each phase and upper and lower limits for the amount of each element that may be present in each of the listed phases;

identifying the elements present in the region of interest of the sample at a plurality of point locations;

obtaining an electron backscatter diffraction (EBSD) pattern at each of the plurality of point locations in the region of interest;

determining the location of and characteristics of the bands in the EBSD pattern (EBSP);

applying a chemical filter by comparing the amounts of each element at each point against the upper limits and lower limits for a given element with each of the phases in the list of phases to determine a set of possible phases for the point;

assigning a phase to each point by comparing the EBSD band locations and characteristics against the structure parameters for each of the possible phases and determining the best match; and determining the crystallographic orientation of the phase at each of the plurality of point locations in the region of interest.

2. The method of claim 1, wherein the plurality of points are prescribed in a grid of points across a surface of the sample.

3. The method of claim 2, wherein the prescribed grid of points forms a shape selected from a square, a rectangle, a hexagon, a circle, an irregular shape, a randomly determined shape, a shape made up of point locations determined from information from a secondary image and a shape made up of point locations determined from information from a backscattered image.

4. The method of claim 1, wherein the amounts of each element are measured by energy dispersive spectroscopy (EDS) by counting the number of counts detected for X-ray energies associated with a the spectral fingerprint for each element.

5. The method of claim 1, wherein the characteristics of the bands in the EBSP comprise the intensity of the bands, the geometrical position in the pattern and the width of the bands.

6. The method of claim 1, wherein the EBSP is obtained by using an instrument selected from the group consisting of scanning electron microscopes (SEM), microprobe analyzers, and dual beam focused ion beam/SEM instruments.

7. The method of claim 1, wherein the sample is a crystalline sample having crystallographic symmetry.

8. The method of claim 1, wherein the location of the bands in the EBSP are determined using a method selected from one or more of the Hough transform, the Radon transform, and the Burns algorithm.

9. The method of claim 1, wherein the location of each point on the sample, the elemental composition of each respective point, the phase of each respective point, and the crystallographic orientation at each respective point is recorded in a file.

10. The method of claim 9, wherein the steps in the method and the recordation at each point are automated.

11. The method of claim 1, further comprising the step of generating a phase map, wherein each phase is designated by a different color or shade of gray.

12. A method of distinguishing crystalline phases in a polycrystalline sample comprising:

(a) providing a sample;

(b) selecting a region of interest on the sample;

(c) providing a list of phases that may be present in the region of interest to include crystallographic structural parameters for each phase and upper and lower limits for the amount of each element that may be present in each of the listed phases;

(d) identifying the elements present in the region of interest;

(e) prescribing a grid of points across a surface of the sample;

(f) selecting a point on the grid;

(g) applying an electron beam to the point;

(h) obtaining an EBSP;

(i) determining the location of and characteristics of the bands in the EBSP;

(j) measuring the amounts of each element in (d) at the point;

(k) recording the location of the point on the sample, the EBSD band locations and characteristics in (i) and the amounts of each element in (j) as a line in a scan grid file;

(l) repeating (f) through (k) for each point on the prescribed grid to generate a complete scan grid file;

(m) selecting a line from the scan grid file;

(n) applying a chemical filter by comparing the amounts of each element against the upper limits and lower limits for a given element with each of the phases in the list of phases in (c) to determine a set of possible phases for the point;

(o) assigning a phase to the point by comparing the EBSD band locations and characteristics against the structure parameters for each of the possible phases and determining the best match;

(p) determining the crystallographic orientation of the phase at the point;

(q) recording the point location, elemental composition, assigned phase, and crystallographic orientation in a phase grid file;

(r) repeating (m) through (q) for each line in the scan grid file.

13. The method of claim 12, wherein the characteristics of the bands in the EBSP comprise the intensity of the bands, the geometrical position in the pattern and the width of the bands.

14. The method of claim 12, wherein the amounts of each element are measured by energy dispersive spectroscopy (EDS) by counting the number of counts detected for X-ray energies associated with a the spectral fingerprint for each element.

15. The method of claim 12, wherein the EBSP is obtained by using an instrument selected from the group consisting of scanning electron microscopes (SEM), microprobe analyzers, and dual beam focused ion beam/SEM instruments.

16. The method of claim 12, wherein the sample is a crystalline sample having crystallographic symmetry.

17. The method of claim 12, wherein the elemental composition of the sample at each point is determined by a method selected from energy dispersive spectroscopy, wavelength dispersive spectroscopy, and cluster analysis.

18. The method of claim 12, wherein the information used to determine the elemental composition of the sample at each point is selected from counts of X-rays within specified energy ranges correlated to specific chemical elements and energy spectra.

19. The method of claim 12, wherein the prescribed grid of points forms a shape selected from a square, a rectangle, a hexagon, a circle, an irregular shape, a randomly determined shape, a shape made up of point locations determined from information from a secondary image and a shape made up of point locations determined from information from a backscattered image.

20. The method of claim 12, wherein the location and characteristics of the bands in the EBSP is compressed before it is recorded.

21. The method of claim 12, wherein the recording of the location and characteristics of the bands in the EBSP comprises recording specific information about the diffraction bands and data derived from an automated band detection algorithm.

22. The method of claim 12, wherein the crystalline phases in the sample are determined by identifying the phases of all of the points and determining the orientation associated with all of the points.

23. The method of claim 12, wherein the location of the bands in the EBSP are determined using a method comprising the Hough transform.

24. The method of claim 12, wherein the location of the bands in the EBSP are determined using a method comprising the Radon transform.

25. The method of claim 12, wherein the location of the bands in the EBSP are determined using a method comprising the Burns algorithm.

26. The method of claim 12, wherein the steps are automated.

27. The method of claim 12, further comprising the step of generating a phase map, wherein each phase is designated by a different color or shade of gray.

28. A method of distinguishing crystalline phases in a polycrystalline sample comprising:

(a) providing a sample;

(b) prescribing a grid of points across a surface of the sample;

(c) selecting a point on the grid;

(d) applying an electron beam to the point;

(e) determining the elemental composition of the sample at the point;

(f) recording the location of the point on the sample, the EBSD band locations and the elemental composition as a line in a scan grid file;

(g) repeating (c) through (f) for each point on the prescribed grid;

(h) providing a list of phases that may be present in the sample to include crystallographic structural parameters for each phase and upper and lower limits for the amount of each element that maybe present in each of the listed phases;

(i) selecting a line from the scan grid file;

(j) applying a chemical filter by comparing the amounts of each element against the upper limits and lower limits for a given element with each of the phases in the list of phases in (h) to determine a set of possible phases for the point;

(k) applying a collimated electron beam to a point on the sample correlating to the point in the scan grid file;

(l) obtaining an EBSP;

(m) determining the location of and characteristics of the bands in the EBSP;

(n) assigning a phase to the point by comparing the EBSD band locations and characteristics against the structure parameters for each of the possible phases and determining the best match;

(o) determining the crystallographic orientation of the phase at the point;

(p) recording the point location, elemental composition, assigned phase, and crystallographic orientation in a phase grid file; and (q) repeating (i) through (p) for each line from the scan grid file.

29. The method of claim 28, wherein the characteristics of the bands in the EBSP comprise the intensity of the bands, the geometrical position in the pattern and the width of the bands.

30. The method of claim 28, wherein the EBSP is obtained by using an instrument selected from the group consisting of scanning electron microscopes (SEM), microprobe analyzers, and dual beam focused ion beam/SEM instruments.

31. The method of claim 28, wherein the sample is a crystalline sample having crystallographic symmetry.

32. The method of claim 28, wherein the elemental composition of the sample at each point is determined by a method selected from energy dispersive spectroscopy, wavelength dispersive spectroscopy and cluster analysis.

33. The method of claim 28, wherein the information used to determine the elemental composition of the sample at each point is selected from counts of X-rays within specified energy ranges correlated to specific chemical elements and energy spectra.

34. The method of claim 28, wherein the prescribed grid of points forms a shape selected from a square, a rectangle, a hexagon, a circle, an irregular shape, a randomly determined shape, a shape made up of point locations determined from information from a secondary image and a shape made up of point locations determined from information from a backscattered image.

35. The method of claim 28, wherein the location and characteristics of the bands in the EBSP is compressed before it is recorded.

36. The method of claim 28, wherein the recording of the location and characteristics of the bands in the EBSP comprises recording specific information about the diffraction bands and data derived from an automated band detection algorithm.

37. The method of claim 28, wherein the crystalline phases in the sample are determined by identifying the phases of all of the points and determining the orientation associated with all of the points.

38. The method of claim 28, wherein the location of the bands in the EBSP are determined using a method comprising the Hough transform.

39. The method of claim 28, wherein the location of the bands in the EBSP are determined using a method comprising the Radon transform.

40. The method of claim 28, wherein the location of the bands in the EBSP are determined using a method comprising the Burns Algorithm.

41. The method of claim 28, wherein the steps are automated.

42. The method of claim 28, further comprising the step of generating a phase map, wherein each phase is designated by a different color or shade of gray.

43. An instrument for determining the crystallographic aspects of materials comprising:
- a scanning electron microscope that includes a means for applying an electron beam to a sample, a means for obtaining an EBSP, and a means for determining the elemental composition of the sample;
- a means for recording EBSD band locations and characteristics and the elemental composition of the sample; and
- a means to automate the instrument to carry out the steps of:
  - (a) prescribing a grid of points across a surface of the sample;
  - (b) selecting a point on the grid;
  - (c) applying an electron beam to the point;
  - (d) determining the elemental composition of the sample at the point;
  - (e) recording the location of the point on the sample, the EBSD band locations and the elemental composition as a line in a scan grid file;
  - (f) repeating (b) through (c) for each point on the prescribed grid;
  - (g) providing a list of phases that may be present in the sample to include crystallographic structural parameters for each phase and upper and lower limits for the amount of each element that may be present in each of the listed phases;
  - (h) selecting a line from the scan grid file;
  - (i) applying a chemical filter by comparing the amounts of each element against the upper limits and lower limits for a given element with each of the phases in list of phases in (g) to determine a set of possible phases for the point;
  - (j) applying a collimated electron beam to a point on the sample correlating to the point in the scan grid file;
  - (k) obtaining an EBSP;
  - (l) determining the location of and characteristics of the bands in the EBSP;
  - (m) assigning a phase to the point by comparing the EBSD band locations and characteristics against the structure parameters for each of the possible phases and determining the best match;
  - (n) determining the crystallographic orientation of the phase at the point;
  - (o) recording the point location, elemental composition, assigned phase, and crystallographic orientation in a phase grid file; and
  - (p) repeating (h) through (o) for each line from the scan grid file.

44. The instrument of claim 43, wherein the characteristics of the bands in the EBSP comprise the intensity of the bands, the geometrical position in the pattern and the width of the bands.

45. The instrument of claim 43, wherein the a means for determining the elemental composition of the sample are selected from energy dispersive spectroscopy, cluster analysis, wavelength dispersive spectroscopy, analysis of counts of X-rays within specified energy ranges correlated to specific chemical elements and energy spectra.

46. The instrument of claim 43, wherein the location and characteristics of the bands in the EBSP are compressed before being recorded.

* * * * *

UNITED STATES PATENT AND TRADEMARK OFFICE
CERTIFICATE OF CORRECTION

PATENT NO. : 6,835,931 B2
DATED : December 28, 2004
INVENTOR(S) : Wright et al.

It is certified that error appears in the above-identified patent and that said Letters Patent is hereby corrected as shown below:

Column 14,
Line 24, "a the spectral fingerprint" should read -- the spectral fingerprint --

Column 15,
Line 24, "a the spectral fingerprint" should read -- the spectral fingerprint --

Column 16,
Line 24, "maybe present" should read -- may be present --

Column 18,
Lines 15-16, "in list" should read -- in the list --
Line 38, "the a means" should read -- the means --

Signed and Sealed this

Seventh Day of June, 2005

JON W. DUDAS
*Director of the United States Patent and Trademark Office*